US010568753B2

(12) United States Patent
Epstein (10) Patent No.: US 10,568,753 B2
(45) Date of Patent: Feb. 25, 2020

(54) CATHETER OR STENT DELIVERY SYSTEM

(71) Applicant: Scott M. Epstein, Boston, MA (US)

(72) Inventor: Scott M. Epstein, Boston, MA (US)

( * ) Notice: Subject to any disclaimer, the term of this patent is extended or adjusted under 35 U.S.C. 154(b) by 0 days.

(21) Appl. No.: 14/446,893

(22) Filed: Jul. 30, 2014

(65) Prior Publication Data

US 2014/0343684 A1  Nov. 20, 2014

Related U.S. Application Data

(63) Continuation of application No. 12/824,149, filed on Jun. 26, 2010.

(51) Int. Cl.
| | | |
|---|---|---|
| A61F 2/962 | (2013.01) | |
| A61M 25/01 | (2006.01) | |
| A61F 2/04 | (2013.01) | |
| A61M 25/02 | (2006.01) | |
| A61M 25/00 | (2006.01) | |
| A61M 25/06 | (2006.01) | |

(52) U.S. Cl.
CPC ............... *A61F 2/962* (2013.01); *A61F 2/04* (2013.01); *A61M 25/01* (2013.01); *A61F 2002/048* (2013.01); *A61F 2230/0067* (2013.01); *A61F 2230/0071* (2013.01); *A61F 2250/0098* (2013.01); *A61M 25/0021* (2013.01); *A61M 25/0068* (2013.01); *A61M 2025/0293* (2013.01); *A61M 2025/0681* (2013.01)

(58) Field of Classification Search
CPC .................................. A61F 2/95; A61F 2/958
USPC ................. 606/108, 191; 623/1.11
See application file for complete search history.

(56) References Cited

U.S. PATENT DOCUMENTS

| | | | |
|---|---|---|---|
| 3,975,350 A | * | 8/1976 | Hudgin ............... A01N 25/10 524/108 |
| 4,026,296 A | | 5/1977 | Stoy et al. |
| 4,475,972 A | | 10/1984 | Wong |
| 4,585,000 A | | 4/1986 | Hershenson |
| (Continued) | | | |

FOREIGN PATENT DOCUMENTS

WO  0018446 A1  4/2000

OTHER PUBLICATIONS

U.S. Appl. No. 11/590,219, filed Oct. 31, 2006, Granted, U.S. Pat. No. 8,048,350.
U.S. Appl. No. 13/231,752, filed Sep. 13, 2011, Published.

*Primary Examiner* — Richard G Louis
(74) *Attorney, Agent, or Firm* — Intrinsic Law Corp.

(57) ABSTRACT

A method for delivering catheters, and stents composed of soft, compliant polymers through anatomical passages. These devices have a bulbous anchorage end with a diameter greater than the rest of the catheter. To facilitate implant and delivery a pusher catheter or sheath with an internal lumen larger than the outer diameter of the catheter but smaller than the outer diameter of the bulbous anchorage end. The distal end of pusher catheter or the sheath physically engages the proximal end of the bulbous anchorage end and applies an axial force to coaxially advance the catheter over a guidewire though anatomical passages. This method allows a physician to move the catheter to an anatomical site without the device exhibiting buckling due to axial force applied. Similarly, this delivery method will allow more force to be applied to the distal end of the catheter diminishing the likelihood of buckling.

21 Claims, 10 Drawing Sheets

(56) References Cited

U.S. PATENT DOCUMENTS

| | | | |
|---|---|---|---|
| 4,610,671 A * | 9/1986 | Luther | A61M 25/0606 604/168.01 |
| 4,762,128 A | 8/1988 | Rosenbluth | |
| 4,943,618 A | 7/1990 | Stoy et al. | |
| 5,026,366 A | 6/1991 | Leckrone | |
| 5,135,535 A | 8/1992 | Kramer | |
| 5,149,052 A | 9/1992 | Stoy et al. | |
| 5,405,380 A | 4/1995 | Gianotti et al. | |
| 5,499,975 A * | 3/1996 | Cope | A61M 25/0662 604/164.1 |
| 5,499,994 A * | 3/1996 | Tihon | A61F 2/94 604/104 |
| 5,601,881 A | 2/1997 | Grimm et al. | |
| 5,603,698 A * | 2/1997 | Roberts | A61F 2/95 604/104 |
| 5,662,703 A * | 9/1997 | Yurek et al. | 623/1.12 |
| 5,697,948 A | 12/1997 | Marin et al. | |
| 5,785,679 A | 7/1998 | Abolfathi et al. | |
| 6,027,510 A | 2/2000 | Alt | |
| 6,039,694 A | 3/2000 | Larson et al. | |
| 6,143,016 A | 11/2000 | Bleam et al. | |
| 6,280,411 B1 | 8/2001 | Lennox | |
| 6,286,785 B1 * | 9/2001 | Kitchen | 244/121 |
| 6,379,365 B1 * | 4/2002 | Diaz | 606/108 |
| 6,458,156 B1 * | 10/2002 | Wan et al. | 623/2.14 |
| 6,471,684 B2 | 10/2002 | Dulak et al. | |
| 6,488,802 B1 | 12/2002 | Levingston et al. | |
| 6,547,908 B2 | 4/2003 | Keyes et al. | |
| 6,827,731 B2 * | 12/2004 | Armstrong et al. | 623/1.12 |
| 6,926,509 B2 | 8/2005 | Nicora et al. | |
| 7,135,015 B2 | 11/2006 | Dulak et al. | |
| 7,316,677 B1 | 1/2008 | Dulak et al. | |
| 7,622,299 B2 | 11/2009 | Sanders et al. | |
| 7,654,989 B2 | 2/2010 | Knapp | |
| 7,655,021 B2 | 2/2010 | Brasington et al. | |
| 7,713,193 B2 | 5/2010 | Nance et al. | |
| 8,048,350 B2 | 11/2011 | Epstein | |
| 8,101,196 B2 | 1/2012 | Luthra et al. | |
| 8,235,968 B2 | 8/2012 | Tremaglio | |
| 8,282,622 B2 | 10/2012 | Dulak et al. | |
| 8,403,890 B2 | 3/2013 | King et al. | |
| 8,491,620 B2 | 7/2013 | Brasington et al. | |
| 8,597,261 B2 | 12/2013 | Knapp | |
| 8,690,936 B2 | 4/2014 | Nguyen et al. | |
| 8,696,550 B2 | 4/2014 | Surti | |
| 8,708,997 B2 | 4/2014 | Parker | |
| 8,709,064 B2 | 4/2014 | Rasmussen et al. | |
| 2001/0011164 A1 * | 8/2001 | Bierman | A61M 25/02 604/180 |
| 2002/0077592 A1 * | 6/2002 | Barry | 604/96.01 |
| 2002/0082549 A1 * | 6/2002 | Duchamp | A61M 25/1034 604/96.01 |
| 2002/0082638 A1 | 6/2002 | Porter et al. | |
| 2002/0120322 A1 * | 8/2002 | Thompson | A61F 2/91 623/1.11 |
| 2002/0198440 A1 * | 12/2002 | Snow | 600/116 |
| 2003/0021762 A1 | 1/2003 | Luthra et al. | |
| 2003/0040771 A1 * | 2/2003 | Hyodoh | A61F 2/90 606/200 |
| 2003/0109899 A1 * | 6/2003 | Fisher | A61B 17/0057 606/213 |
| 2003/0199993 A1 * | 10/2003 | Gellman | A61L 27/34 623/23.75 |
| 2003/0204238 A1 * | 10/2003 | Tedeschi | 623/1.11 |
| 2003/0211130 A1 | 11/2003 | Sanders et al. | |
| 2003/0216771 A1 | 11/2003 | Osypka et al. | |
| 2003/0222369 A1 | 12/2003 | Nicora et al. | |
| 2003/0233117 A1 * | 12/2003 | Adams | A61F 2/013 606/200 |
| 2004/0010284 A1 * | 1/2004 | Maloof | A61F 9/0017 606/213 |
| 2004/0015224 A1 * | 1/2004 | Armstrong et al. | 623/1.12 |
| 2004/0111143 A1 * | 6/2004 | Fischell | A61F 2/95 623/1.11 |
| 2004/0143290 A1 * | 7/2004 | Brightbill | A61B 17/00491 606/213 |
| 2004/0225346 A1 * | 11/2004 | Mazumder et al. | 623/1.13 |
| 2004/0243158 A1 | 12/2004 | Konstantino et al. | |
| 2005/0033343 A1 * | 2/2005 | Chermoni | A61M 25/0122 606/191 |
| 2005/0038495 A1 * | 2/2005 | Greenan | A61F 2/95 623/1.11 |
| 2005/0049672 A1 * | 3/2005 | Murphy | 623/1.12 |
| 2005/0149160 A1 * | 7/2005 | McFerran | 623/1.11 |
| 2005/0182475 A1 | 8/2005 | Jen et al. | |
| 2006/0095066 A1 * | 5/2006 | Chang | A61B 34/20 606/199 |
| 2006/0100664 A1 * | 5/2006 | Pai | A61B 17/00491 606/214 |
| 2007/0010786 A1 * | 1/2007 | Casey | A61B 17/22031 604/95.04 |
| 2007/0106361 A1 * | 5/2007 | Epstein | 623/1.1 |
| 2007/0208373 A1 * | 9/2007 | Zaver | A61F 2/01 606/200 |
| 2007/0225659 A1 * | 9/2007 | Melsheimer | A61M 25/0668 604/264 |
| 2007/0250160 A1 * | 10/2007 | Rafiee | A61B 17/00234 623/2.11 |
| 2007/0299422 A1 * | 12/2007 | Inganas | A61B 17/0057 604/508 |
| 2008/0255603 A1 * | 10/2008 | Naor et al. | 606/200 |
| 2008/0300629 A1 * | 12/2008 | Surti | A61B 17/0401 606/232 |
| 2009/0299449 A1 * | 12/2009 | Styrc | 623/1.11 |
| 2010/0022940 A1 | 1/2010 | Thompson | 604/9 |
| 2011/0153022 A1 * | 6/2011 | Singhatat | A61F 2/441 623/17.16 |
| 2011/0301689 A1 | 12/2011 | Dorn et al. | |
| 2016/0199620 A1 * | 7/2016 | Pokorney | A61M 25/09 600/585 |

* cited by examiner

CATHETER OR STENT DELIVERY SYSTEM

CROSS-REFERENCE TO RELATED APPLICATION

The present application is a continuation under 35 U.S.C. § 120 of U.S. patent application Ser. No. 12/824,149, filed Jun. 26, 2010, which is incorporated by reference herein in its entirety.

FIELD OF INVENTION

The present invention relates to a catheter delivery method and apparatus for delivering catheters or stents, specifically catheters or stents composed of soft, compliant polymers or other suitable materials, through anatomical passages, vascular networks, lumens and cavities.

BACKGROUND OF INVENTION

Specifically-trained physicians often implant a catheter or stent over a guidewire, proximate to, vascular and non-vascular occlusions; or to maintain patency of an anatomical lumen. To implant these devices, a physician must pass the device through vascular and non-vascular anatomical passages and cavities to reach the intended anatomical site which may exhibit an occlusion or an increased resistance when advancing the catheter or stent to the intended location.

One accepted method for passing these devices through anatomical passages includes placing the distal end (defined as the end that is farthest from the Physician) of a guidewire proximate to the anatomical site and advancing the catheter coaxially over the guidewire. In this method, the catheter is pushed from the proximal (defined as the end closest to the Physician) end of the guidewire to the distal end towards the anatomical site. The catheter is advanced either by hand (squeezing the catheter with an index finger and thumb and pushing along) or by using a relatively rigid plastic tube to push the catheter from behind.

In this method, the catheter must be pushed over the guidewire through long, sometimes tortuous, paths, reductions in lumen diameter and anatomical obstructions. Unfortunately, these obstacles require the physician to push the catheter or stent with increasingly excessive axial forces, and depending on the device design or the material from which the device is fabricated, buckling may occur.

Buckling of the device, due to excessive axial forces, is undesired as it may result in a damaged catheter, patient discomfort, accidental perforation of surrounding anatomy and prevention of catheter implantation to its intended location.

The axial load is the maximum force that may be applied to a catheter or stent when advancing the device into a patient before it begins to buckle. Therefore, the axial load is limited by the column strength of the device. This axial load is characterized by the Euler Equation for a simply supported device column under an external axial load (F); wherein (E=modulus of elasticity of the device; I=is the moment of inertia of the cross section of the device; and L=column length of the device). Accordingly, the buckling load of a catheter or stent can be determined by:

$$F=((E)*(I)(3.14)^2)/(L^2)$$

With respect to the Euler Equation, if Length (L), and Moment of Inertia (I) are constant, only a change in materials with an increase in modulus of Elasticity (E) will increase the axial load capacity of a catheter or stent. For example, using the above Euler Equation, pushing a catheter with a length of (0.5 inches (L=0.50 inch)); compared to a catheter with a length of (12 inches (L=12.0 inch)) exhibits a profound effect on the axial load capacity (F). Considering that (L) is raised to the power of (2); it can be seen that (0.50 inches)$^2$ versus (12 inches)$^2$=0.25 versus 144; or a factor of over 500:1. Thus, devices with shorter columns will have a much greater axial load capacity resisting bucking. Unfortunately, shorter catheters are not practical; nor are they typically used in conventional applications where pushing a catheter is the method of delivery.

Multiple techniques have been developed by physicians to prevent buckling of the catheter during implantation. Many of the techniques mentioned below are often combined to reduce catheter buckling.

One technique is for physicians to apply only small amounts of axial force to the catheter either manually (by hand) or with a plastic tube (pusher catheter). This small axial force results in advancing the catheter several millimeters at a time. While this slow advance of the catheter does provide immediate tactile feedback to the physician should the catheter confront an obstruction during advancement, the process is long and tedious. In addition, once the catheter reaches the vascular occlusion at the implantation site, additional axial forces still must be applied in order to push the catheter across the occlusion. This increased axial force often causes the catheter, especially smaller diameter devices, to buckle.

An additional technique to prevent buckling of a catheter during implantation is to use a catheter or stent that is coated with layers of a lubricous polymer. These lubricous polymer coatings, which are typically are very thin, and relatively fragile, reduce the coefficient of friction of the device, which results in a reduced axial load. When these coated devices are inserted and advanced through anatomical paths, they encounter boundaries, such as vessel walls. These coated devices, which are flexible enough to bend tangentially at these boundaries, continue advancing along the anatomical path; however, these tangential bends may add external pressure to the coating at the points of contact. These external pressure points on the device contribute to the aqueous media being squeezed from the coating, much like squeezing water from a sponge. Ultimately, once the coating is compromised, any further contact between the device and anatomical boundaries at these tangential bends will exhibit an increased level of relative friction, such as dry on dry surfaces that results in increased axial loads required to push or advance the catheter along. In addition, this high friction may result in patient discomfort.

A further technique to prevent buckling of the catheter during implantation is to fabricate whole or portions of catheters and stents from moderate to rigid polymers. Similarly, a given thickness of rigid polymer can be extruded while a softer layer is coaxially extruded over or under the more rigid layer. Additionally, a layer of braiding material, either polymeric and or metallic, may be incorporated into the design of a catheter or stent whereby the braid is deposited or sandwiched between layers of catheter material. While these designs are more effective they result in undesirable and uncomfortable products as well as increased manufacturing costs.

Catheters or stents may also be manufactured with rigid portions, such as rigid proximal ends. These more rigid materials often cause patient discomfort and in many cases result in complications due to their increased ability to perforate surrounding anatomy during implantation.

Conventional delivery methods may also include coaxially placing and advancing soft catheters or stents within hollow rigid sheaths, avoiding the need to develop or design catheters that by themselves exhibit superior handling.

In any case, using a sheath or manufacturing a catheter out of more rigid material or incorporating a layer of braiding material are only attempts to increase the column strength of a catheter or stent whereby axial forces and corresponding push-ability can be maximized.

However, using a more rigid material either as part of the catheter, stent or sheath still results in patent pain and or discomfort.

As mentioned previously, many of the techniques mentioned above are often combined to reduce catheter buckling. For instance, in an attempt to augment conventional sheath-over-catheter delivery methods, catheters may be coaxially braided, a more rigid layer maybe integrated, and/or the device may be coated with layers of lubrious polymer. However, even a combination of these techniques results in patient discomfort, slow advancement and eventual buckling of the catheter or stent when increased axial loads are required to advance into or through anatomical passages.

Therefore, it is the purpose of this invention to establish a novel method for delivery of catheters and stents that overcomes the buckling phenomena.

SUMMARY OF INVENTION

There are additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

The subject invention discloses a method for delivering a catheter or stent to an anatomical site, the method comprising: a) inserting a guidewire into a patient, such that a distal end of the guidewire is proximal to the anatomical site and a proximal end of the guidewire is accessible to a user; b) placing a catheter with an internal channel with a first opening on the distal end and a second opening on a proximal end over the guidewire such that the guidewire is contained within the internal channel, wherein the proximal end of catheter comprises a first external diameter and the distal end comprises a second external diameter, further wherein the second external diameter is larger than the first external diameter such that the distal end of the catheter comprises a proximal external contacting surface; c) placing a tube, sheath, or Pusher catheter with a distal opening and an internal channel over the proximal end of the catheter, wherein the diameter of the distal opening and the internal channel is larger than the first external diameter, but smaller than the second external diameter, further wherein the tube, sheath, or Pusher catheter comprises a distal contacting surface and a proximal pushing surface; d) pushing the tube, sheath, or Pusher catheter over the catheter until the distal contacting surface of the tube engages the proximal external contacting surface of the catheter; e) applying axial force to the proximal pushing surface of the tube, sheath, or Pusher catheter such that it advances the catheter on the guidewire; f) stopping step e) once the catheter or stent is positioned in the anatomical site; and g) removing the tube, sheath or pusher catheter and leaving the catheter or stent in place.

Another embodiment of the subject invention is a catheter delivery system comprising: a catheter with an internal channel with a first opening on the distal end and a second opening on a proximal end, wherein the proximal end of catheter comprises a first external diameter and the distal end comprises a second external diameter, further wherein the second external diameter is larger than the first external diameter such that the distal end of the catheter comprises a proximal external contacting surface; a tube with a distal opening, a distal contacting surface and an internal channel, wherein the diameter of the distal opening and the internal channel is larger than the first external diameter of the catheter, but smaller than the second external diameter; wherein the proximal end of the catheter is place into the distal opening of the tube until the distal contacting surface engages the proximal external contacting surface, further wherein the tube pushes the catheter such that both advance over a guidewire that is inserted into a patient such that a distal end of the guidewire is proximal to an anatomical site.

In one embodiment of the subject invention, the shape of the internal channel of the tube, sheath, or Pusher catheter complements the external shape of the proximal end of the catheter.

In another embodiment of the subject invention, the catheter has a cross-sectional shape that is substantially circular, triangular, square, oval, trapezoidal, hexagonal or octagonal.

In an additional embodiment of the subject invention, the shape of the internal channel of the tube, sheath, or Pusher catheter has a cross-sectional shape that is substantially circular, triangular, square, oval, trapezoidal, hexagonal or octagonal.

In a further embodiment of the subject invention, the tube, sheath, or Pusher catheter is composed of substantially resilient material.

In one embodiment of the subject invention, the distal end of the catheter is a bulbous anchorage end.

In another embodiment of the subject invention, the catheter is composed of a soft compliant material, such as structural hydrogel.

In one embodiment of the subject invention, the method does not require that the guidewire by hydrophilically coated to exhibit a reduction in forces.

In another embodiment of the subject invention, the catheter has at least one port hole proximal to the distal end.

In an additional embodiment of the subject invention, the distal end of the catheter has a profile that is selected from the group consisting of substantially spherical, substantially oval, substantially barbell, substantially trumpet or substantially conical.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto. These together with other objects of the invention, along with the various features of novelty, which characterize the invention, are pointed out with particularity in the claims annexed to and forming a part of this disclosure.

BRIEF DESCRIPTION OF THE DRAWINGS

Advantages of the present invention will be apparent from the following detailed description of exemplary embodiments thereof, which description should be considered in conjunction with the accompanying drawings, in which.

DETAILED DESCRIPTION OF PREFERRED EMBODIMENTS

While several variations of the present invention have been illustrated by way of example in particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth.

The subject invention is a novel method for delivery of catheters and stents to anatomical sites that prevents buckling of the device due to applied axial force.

Figure 1:
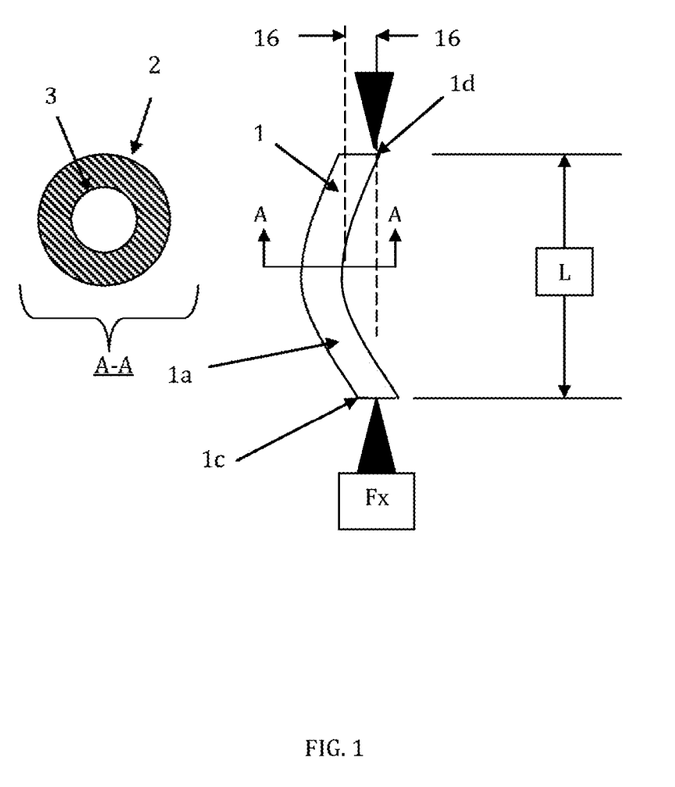
FIG. 1 illustrates a top view and a cross-sectional view of a catheter or stent with simple column catheter shaft with a given length that is subjected to an axial force.
Figure 2:
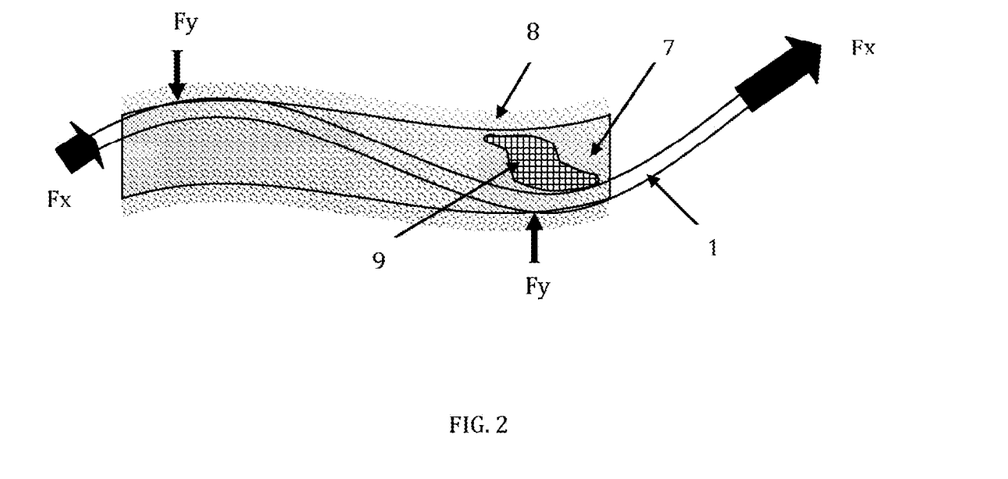
FIG. 2 illustrates a cross-sectional top view of a catheter passing through anatomical lumens upon application of axial force.

FIG. 1 is a diagram illustrating a top view and a cross-sectional view of a catheter or stent (1) with simple column catheter shaft (1a) with a given length (L). An axial force (Fx) may be applied to either the proximal end (1c) of catheter (1) by a physician, the distal end (1d) by an anatomical obstruction, or both when the physician continues to push the catheter (1) once it encounters an anatomical obstructions. As shown in FIG. 2, catheter (1) passes through anatomical lumens (7) upon application of axial force (Fx) to the proximal end of the catheter.

During this passage, the catheter (1) may often contact a wall or peripheral structure (8) of lumen (7) or an obstruction (9). Once this contact occurs, a resulting force (Fy) may be applied to the catheter (1) at tangent points, requiring the application of additional axial force (Fx) to continue advancing the catheter (1) to its intended location.

As shown in FIGS. 1 and 2, the axial force Fx applied to catheter (1) is greater than the axial load, causing the catheter to buckle. Lines (16a) and (16b) illustrate the original position of catheter shaft (1a) prior to buckling.

FIG. 1 further illustrates a cross-sectional view of catheter shaft (1a) delineated by line A-A. Catheter shaft (1a) comprises an outer diameter (2) and an inner diameter (3). Diameters (2) and (3) are used to calculate Moment of Inertia (I) for the Euler Equation.

Figure 9:
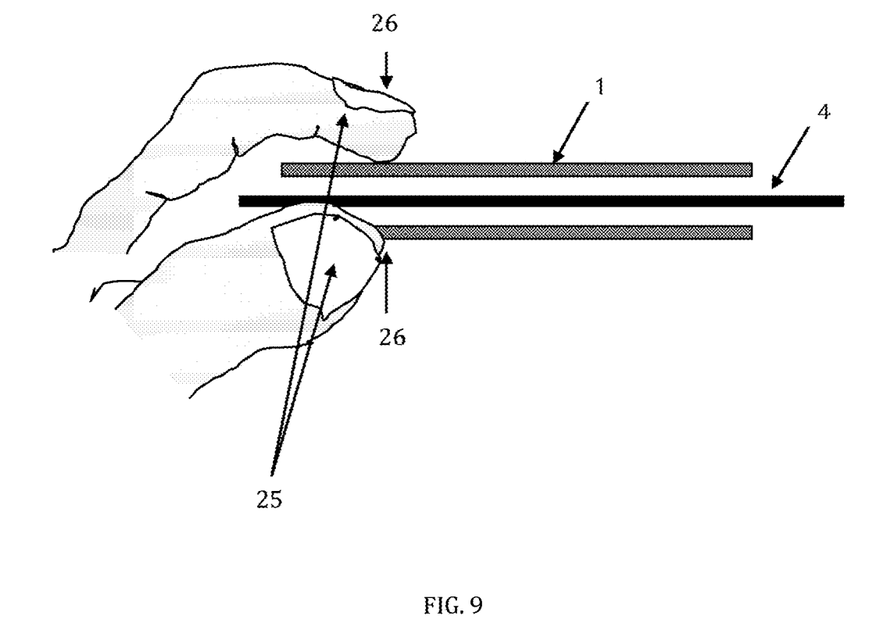
FIG. 9 illustrates a top cross-sectional view of a catheter being pushed by hand over a guidewire.

FIG. 9 illustrates a method of implanting a catheter (1) by squeezing (26) the catheter (1) with a hand (25) and manually advancing the catheter (1) over a guidewire (4) by applying an axial force to coaxially advanced the catheter over the guidewire (4) in a distal direction though anatomical passages (not shown).

Figure 3:
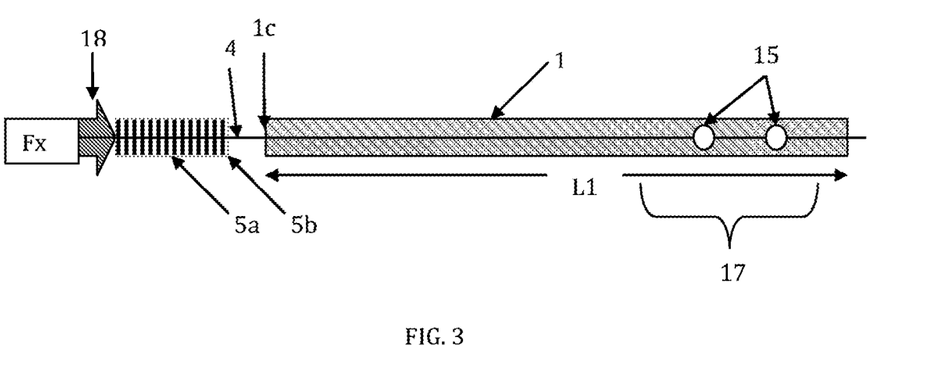
FIG. 3 illustrates a top view of a conventional method of implanting a catheter of length.

FIG. 3 illustrates a conventional method of implanting a catheter (1) of length (L1). Catheter (1) is coaxially slid over a guidewire (4). A distal end (5b) of a pusher catheter (5a) physically engages the proximal end (1c) of the catheter (1) and applies an axial force (Fx) to coaxially advanced the catheter over the guidewire (4) in a distal direction (18) though anatomical passages (not shown).

In this conventional method, pusher catheter (5a) has an internal lumen (not shown) with an internal diameter that is large enough to allow the guidewire (4) to pass through pusher catheter (5a) as it advances; however, this internal lumen diameter is smaller than outer diameter (2) of catheter (1) to allow the distal end (5b) of pusher catheter (5a) to engage the proximal end (1c) of the catheter (1).

FIG. 3 further illustrates two catheter port holes (15) located proximal to the distal end of the catheter (1). These port holes (15) in conventional catheters are designed to increase fluid transfer within the catheter. However, these port holes (15) often result in increased likelihood of buckling, as shown as the likely buckling point (17).

Figure 4:
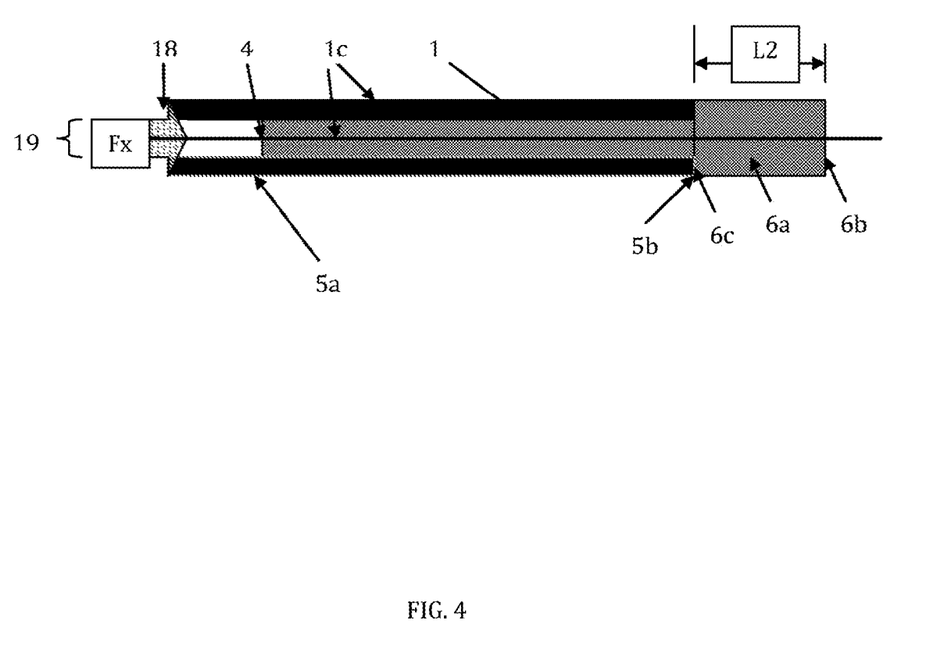
FIG. 4 illustrates a top cross-sectional view of a catheter with a bulbous anchorage end being pushed over a guidewire by the physical engagement of the distal end of a pusher catheter and the proximal end of the bulbous anchorage end.

FIG. 4 illustrates an embodiment of a method of the subject invention. A catheter or stent (1) is coaxially slid over the guidewire (4). In this embodiment, the catheter (1) has a bulbous anchorage end (6a). The bulbous anchorage end (6a) has a distal end (6b) and a proximal end (6c) separated by a length (L2). The bulbous anchorage end (6a) has an outer diameter that is greater than outer diameter (2) of the catheter (1).

In this embodiment, the pusher catheter (5a) has an internal lumen (not shown) with an internal diameter (19) that is large enough to allow the guidewire (4) and the outer diameter (2) of catheter (1) to pass through pusher catheter (5a) as it advances. However, this internal lumen diameter is smaller than the outer diameter of the bulbous anchorage end (6a) of catheter (1). Thus, the distal end (5b) of pusher catheter (5a) physically engages the proximal end (6c) of the bulbous anchorage end (6a) and applies an axial force (Fx) to coaxially advanced the catheter (1) over the guidewire (4) in a distal direction (18) though anatomical passages (not shown). In this manner only a short column length (L2) of the bulbous anchorage end (6a) of catheter (1) has an axial load applied to it, a critical variable in column strength analysis.

This physically engagement between the distal end (5b) of pusher catheter (5a) and the proximal end (6c) of the bulbous anchorage end (6a) diminishes the likelihood of buckling compared to a similar axial force applied to the proximal end (1c) as shown in FIG. 3. Since this method allows the application of additional axial force without buckling, a physician my push catheter (1) through an obstruction. Accordingly, the disclosed delivery method is a universal system which can be used on any catheter or stent with a distal end that a diameter greater than the shaft diameter of the device. This system diminishes the need for thicker, more rigid catheters. Furthermore, the disclosed invention improves the implantation of catheters comprised of sufficiently soft durometer materials or catheters with ratios of inner diameters and outer diameters that diminish catheter column strength.

This method allows a physician to move the catheter to an anatomical site with less applied axial force over a guidewire since the catheter has less resistance. This method allows a physician to push a relatively short length of catheter rather than a long length. This delivery method will allow more force to be applied to the short distal end of the catheter diminishing the likelihood of buckling.

In one embodiment of the subject invention, the catheter (1) may have port holes, similar to those shown in FIG. 3, immediately proximal (not shown) to the bulbous anchorage end (6a) that do not affect buckling of the device. In this embodiment, the internal lumen of the pusher catheter (5a) will pass over the port holes contained on the outer diameter (2) of catheter (1) to physically engage the proximal end (6c) of the bulbous anchorage end (6a).

Figure 5:
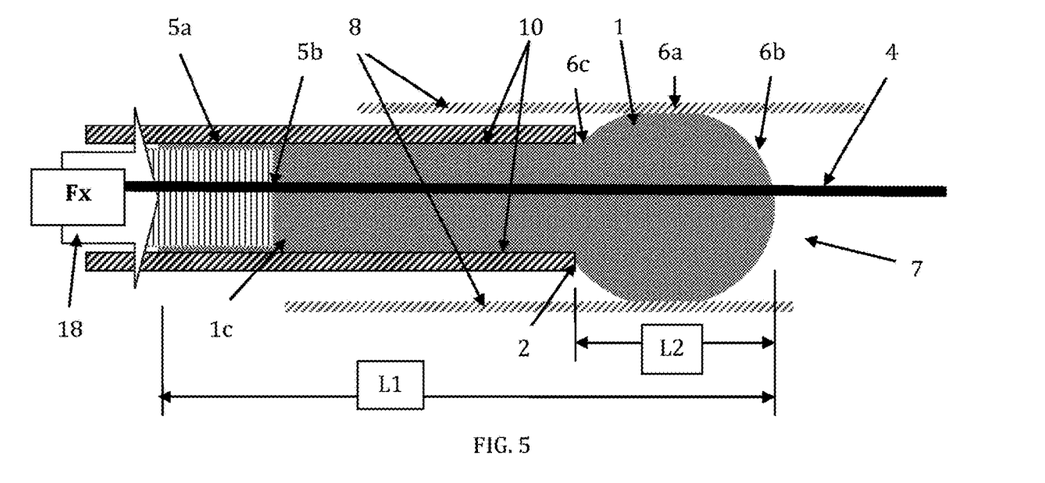
FIG. 5 illustrates a top cross-sectional view of a catheter with a bulbous anchorage end being pushed out of a sheath over a guidewire by the physical engagement of the distal end of a pusher catheter and the proximal end of the bulbous anchorage end.

FIG. 5 illustrates another embodiment of a method of the subject invention. In this embodiment, a catheter or stent (1) is coaxially slid over the guidewire (4). The catheter (1) has a bulbous anchorage end (6a). The bulbous anchorage end (6a) has a distal end (6b) and a proximal end (6c) separated by a length (L2). The bulbous anchorage end (6a) has an outer diameter that is greater than outer diameter (2) of the catheter (1). As shown, the outer diameter (2) of the catheter (1) is contained within a sheath (10) and the bulbous anchorage end (6a) is not contained within the sheath (10). To facilitate delivery of the catheter (1) through anatomical obstructions (illustrated by lumen (7) surrounded by walls (8)), the outer diameter (2) and bulbous anchorage end (6a) of the catheter (1) are both initially contained within sheath (10) (not shown). Once the anatomical site is reached, a distal end (20) of sheath (10) physically engages the proximal end (6c) of the bulbous anchorage end (6a) while within the sheath (10) and applies an axial force (Fx) to coaxially advanced the catheter (1) over the guidewire (4) in a distal direction (18) to push the catheter (1) out of the distal end (20) of the sheath (10) into lumen (7). The pusher catheter (5a) has an internal lumen (not shown) with an internal diameter (19) that is large enough to allow the guidewire (4) to pass through pusher catheter (5a) as it advances. In another embodiment of the subject invention, distal end (5b) of pusher catheter (5a) may also physically engage the proximal end (1c) of the catheter (1) and apply an axial force (Fx) to coaxially advance the catheter (1) over the guidewire (4) out through the distal end (20) of sheath (10) once the anatomical site is reached.

Figure 6:
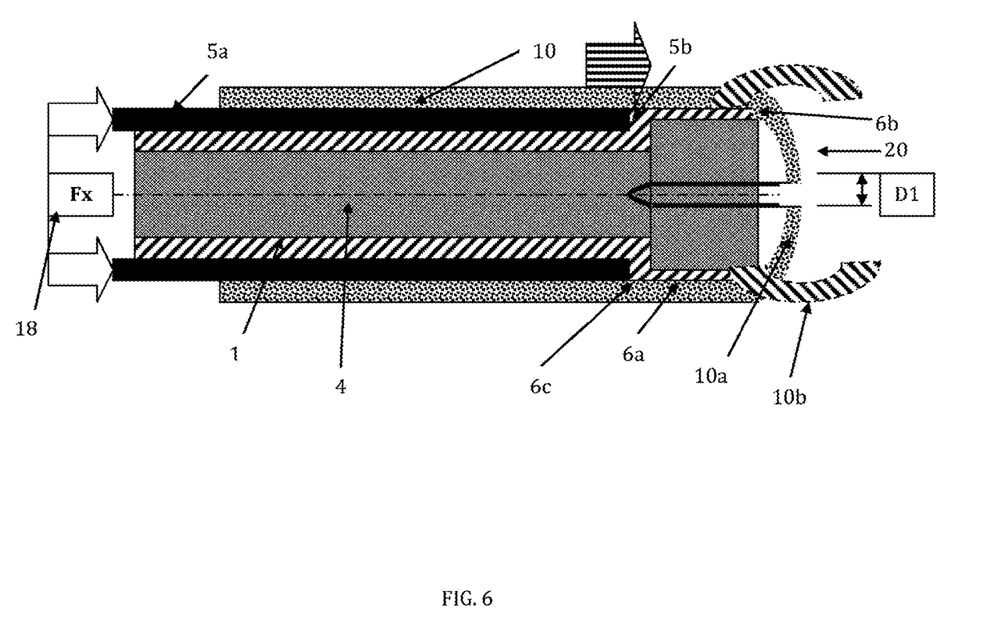
FIG. 6 illustrates a top cross-sectional view of a catheter with a bulbous anchorage end and a pusher catheter contained within a sheath that comprises a substantially spherical distal end that remains closed to facilitate advancement through anatomical obstructions, wherein once the desired site is reached, the distal end of a pusher catheter engages the proximal end of the bulbous anchorage end to push the catheter out of the distal end of the sheath.

FIG. 6 illustrates an alternative embodiment of a method of the subject invention. In this embodiment, a catheter or stent (1) has a bulbous anchorage end (6a) with a distal end (6b) and a proximal end (6c). The bulbous anchorage end (6a) has an outer diameter that is greater than outer diameter (2) of the catheter (1). A pusher catheter (5a) has an internal lumen (not shown) with an internal diameter that is large enough to allow the outer diameter (2) of catheter (1) to pass through pusher catheter (5a) as it advances. However, this internal lumen diameter is smaller than the outer diameter of the bulbous anchorage end (6a) of catheter (1). Thus, the distal end (5b) of pusher catheter (5a) physically engages the proximal end (6c) of the bulbous anchorage end (6a). The outer diameter (2) of the catheter and the bulbous anchorage end (6a) are both coaxially slid and contained within sheath (10). Sheath (10) has a closed end (10a) with by axial slits of a corresponding thickness (D1). The catheter (1), the pusher catheter (5a) and the stent (10) are all coaxially slid over a guidewire (4). The distal end (5b) of pusher catheter (5a) physically engages the proximal end (6c) of the bulbous anchorage end (6a) and applies an axial force (Fx) to coaxially advance the catheter (1) and the sheath (10) over the guidewire (4) in a distal direction (18). Once the anatomical site is reached, the distal end (5b) of pusher catheter (5a) physically engages the proximal end (6c) of the catheter (1) and applies an axial force (Fx) to coaxially advance the catheter (1) over the guidewire (4) out through sheath (10). The axial slits open (10b) to allow catheter or stent (1) to coaxially slide over the guidewire (4) and through sheath (10). A pusher catheter (5a) within a sheath (10) with a closed end adds greater stability when pushing the catheter through difficult and occluded passages.

Figure 7A:
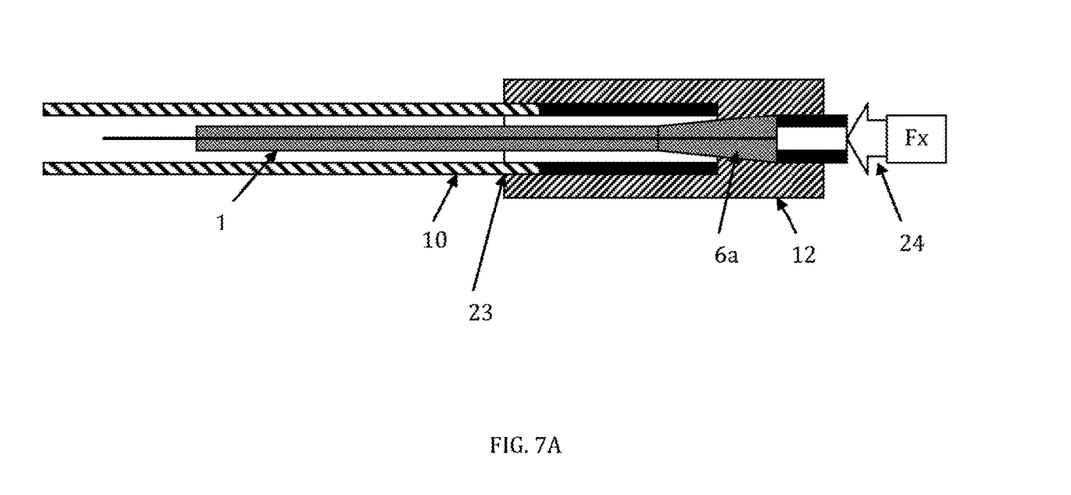
FIGS. 7A-C illustrate a top cross-sectional view of a catheter with a bulbous anchorage end being pushed out of a sheath over a guidewire by the physical engagement of the distal end of a pusher catheter and the proximal end of the bulbous anchorage end.
Figure 7B:
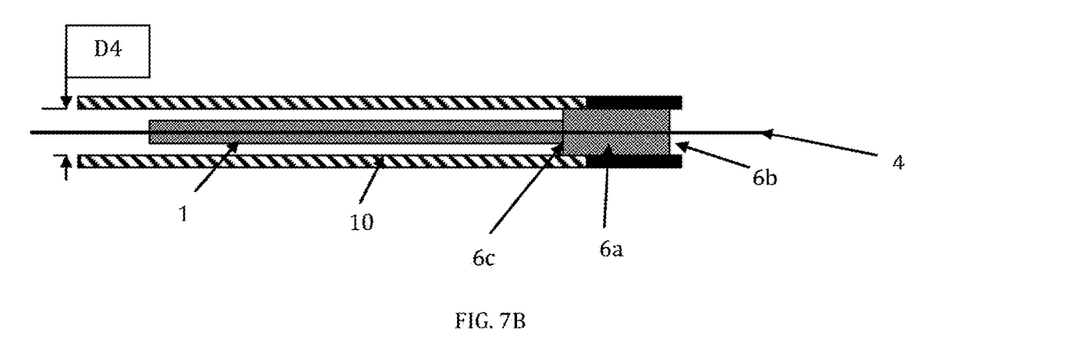
Figure 7C:
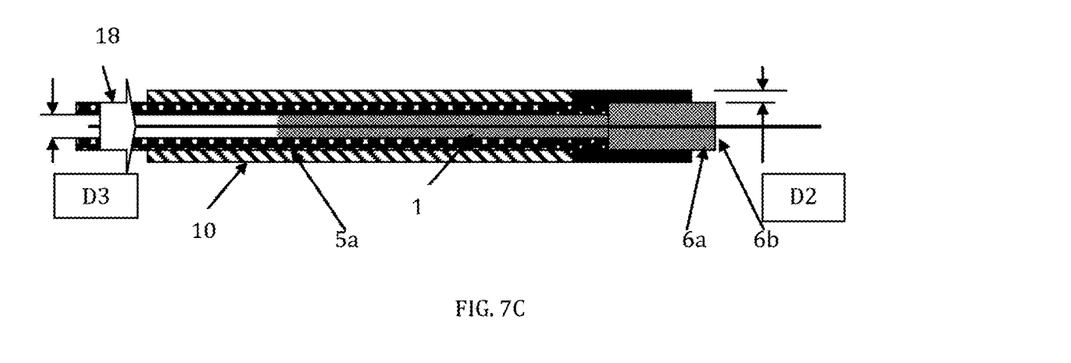

FIGS. 7A-C illustrates another embodiment of a method of the subject invention. A catheter or stent (1) is loaded or facilitated into a sheath (10) thru a loading fixture (12). A loading fixture (12) contains a lumen (23) with distal and proximal openings. The proximal opening of loading fixture (12) has an internal diameter that is greater than the external diameter of sheath (10). The distal end of sheath (10) is inserted in the proximal opening of loading fixture (12). The proximal end of catheter (1) is then inserted into the distal opening of loading fixture (12) by applying an axial force (24) to the distal end (6b) of the catheter. Catheter (1) passes through the internal lumen of fixture (12) and inserts into in internal diameter (D4) of sheath (10) until the bulbous anchorage end (6a) (collapses and) is fully contained within sheath (10). A pusher catheter (5a) has an internal lumen (not shown) in inserted into the proximal end of sheath (10). Pusher catheter (5a) has an internal diameter (D3) that is large enough to allow the outer diameter (2) of catheter (1) to pass through pusher catheter (5a) as it advances. However, this internal lumen diameter is smaller than the outer diameter of the bulbous anchorage end (6a) of catheter (1). Thus, the distal end (5b) of pusher catheter (5a) physically engages the proximal end (6c) of the bulbous anchorage end (6a). The outer diameter (2) of the catheter and the bulbous anchorage end (6a) are both coaxially contained within sheath (10). Once the anatomical site is reached, the distal end (5b) of pusher catheter (5a) physically engages the proximal end (6c) of the bulbous anchorage end (6a) and applies an axial force (Fx) to coaxially advance the catheter (1) over the guidewire (4) in a distal direction (18) out through sheath (10).

Figure 8:
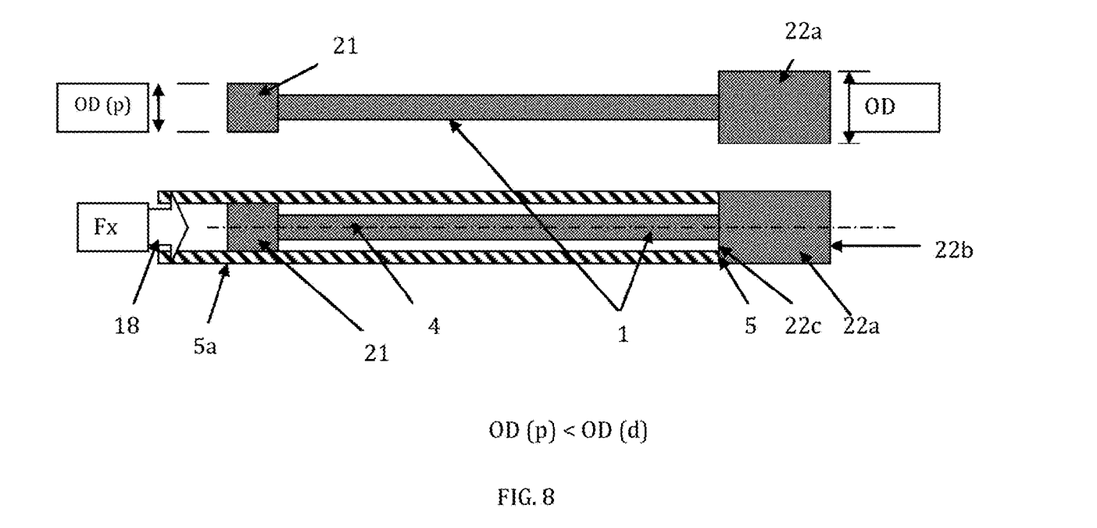
FIG. 8 illustrates a top cross-sectional view of a catheter with a bulbous proximal end anchor and a bulbous distal end anchor (of larger diameter than the bulbous proximal end anchor diameter), being pushed over a guidewire by the physical engagement of the distal end of a pusher catheter and the proximal end of the bulbous distal end anchor.

FIG. 8 illustrates a top cross-sectional view of a catheter (1) with a bulbous proximal end anchor (21) with an outer diameter (OD (p)) and a bulbous distal end anchor (22a) with an outer diameter (OD (d). The distance between bulbous proximal end anchor (21) and the bulbous distal end anchor (22a) has a diameter (2). The outer diameter (OD (p)) is slightly smaller that outer diameter (OD (d)), which are both larger than diameter (2). The bulbous distal end anchor (22a) has a distal end (22b) and a proximal end (22c).

A pusher catheter (5a) has an internal lumen (not shown) with an internal diameter that is large enough to allow the guidewire (4), the outer diameter (2) and the outer diameter (OD (p)) of the bulbous proximal end anchor to pass through pusher catheter (5a) as it advances. However, this internal lumen diameter is smaller than the outer diameter of the bulbous distal end anchor (22a) of catheter (1). Thus, the distal end (5b) of pusher catheter (5a) physically engages the proximal end (22c) of the bulbous distal end anchor (22a) and applies an axial force (Fx) to coaxially advanced the catheter (1) over the guidewire (4) in a distal direction (18) though anatomical passages (not shown).

Figure 10:
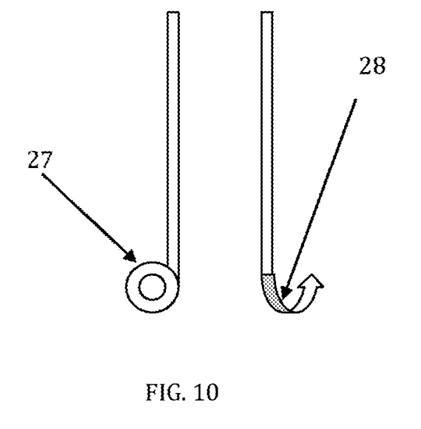
FIG. 10 illustrates a top view of a conventional pigtail loop catheter and a "J" loop catheter.

As shown in FIG. 10, Ureteral stents often have this type of proximal and distal anchorage ends. However, conventional Ureteral stents typically have an end with a spiral or "pigtail" loop (27) configuration, or a "J" shaped loop (28) configuration.

This method of delivery will reduce the pain and discomfort in patients caused by the deformation of Pigtail loop (27) and J shaped loop (28) during catheter implantation. This pain is partially due to the winding and unwinding of the pigtail loop (27) or J shaped loop (28) during implantation. Unfortunately, as these loops unwind to about half the circumference of the loop diameter, the loops become stuck in that configuration. Thereafter, the radial forces which project from the re-configured loops subject the patient to pain, and discomfort.

In various embodiments of the subject invention, the sheath or pusher catheter may have radiopaque ends.

In other embodiments of the subject invention, the anchorage end of the catheter or stent may have a spherical, oval, barbell, trumpet or conical profile.

In another embodiment of the subject invention, the stent or catheter used in the method may be composed entirely or partially of soft hydrogel polymer layers, such as the soft hydrogel ureteral stents disclosed in Epstein, U.S. Published Patent Application No. 2007/0106361. The contents of Epstein are incorporated herein by reference.

These devices are composed entirely of, or have integral components, such as the bulbous anchorage end, composed entirely of 100% hydrogel layers. The hydrogel is an integral component comprising the stent or catheter, not a coating that may erode during passage through anatomical lumens.

These hydrogel devices may also be implanted with a substantially smaller diameter that is partially or totally dehydrated. In this manner the ratio of proximal to distal diameters is typical to the fully hydrated devices whereby a pusher catheter may still coaxially slide over the proximal end diameter and engage a slightly larger distal end diameter. Upon reaching the anatomical site, these highly hydrophilic devices are then hydrated with a significant volume of an aqueous media, such as saline. Upon hydration, the hydrogel cross sections of these devices expand into predictable larger, soft, easily compressible and structurally stable shapes that maintain their mechanical integrity.

These devices do not erode and do not require a substrate or scaffold to maintain their composition or mechanical characteristics. Substantial mechanical characteristics are exhibited by fully hydrated devices, which can be loaded with colorants, radiopacifiers and fillers. These devices immediately exhibit lubricous surface characteristics when wetted with any aqueous media and provide increased resistance to biological complications, such as physiological rejection or inflammation, once implanted. The anchorage ends of these devices will not migrate will exhibit resistance to encrustation and will facilitate the ease of implant and withdrawal.

Furthermore, hybrid designs utilizing a hydrogel component and non-hydrogel components can be engineered with different percent concentrations of solids in a specific layer, or positioned specifically along the axis of a catheter shaft. In this manner radiopaque media can be placed where it is desired, or a denser matrix can be produced in specific layers along the axis, providing a differential gradient that promotes diffusion or conduction enhancing drainage, or providing a specific drug delivery barrier.

In other embodiment of the subject invention, a low profile balloon may be integrated into the catheter, either within or external to the bulbous anchorage end.

What is claimed is:

1. A catheter or stent delivery system that reduces buckling of a catheter or stent during delivery through an anatomical lumen to a target site, the catheter or stent delivery system comprising:
 a catheter or stent configured to maintain a flow path through an anatomical lumen and maintain patency thereof, the catheter or stent comprising a hydrogel material and including:
  a first portion including a first opening at a first end of the catheter or stent, the first portion having a first external diameter measured as the uncompressed maximum external diameter of the first portion;
  a second portion including a second opening at a second end of the catheter or stent and including a first contacting surface on a proximal end of the second portion, the second portion having a second external diameter measured as the uncompressed maximum external diameter of the second portion, the second external diameter being larger than the first external diameter, and a length of the second portion being shorter than a length of the first portion, wherein the uncompressed maximum external diameter of the second portion is disposed at a distal end of the second portion, the distal end corresponding to the second end of the catheter or stent; and
  an internal channel extending along a channel axis connecting the first opening and the second opening, the internal channel configured to form the flow path through the anatomical lumen, wherein when hydrated, wherein the structural integrity of the catheter or stent is provided by the hydrogel material; and
 a tube including:
  a distal end including a distal opening and a second contacting surface; and
  an internal channel extending along a tube channel axis through the tube and connecting to the distal opening, the internal channel of the tube having a tube channel diameter larger than the catheter or stent first external diameter and smaller than the catheter or stent second external diameter;
 the catheter or stent and tube configured such that, when the first portion of the catheter or stent is positioned within the tube and at least the second portion of the catheter or stent is positioned in an anatomical lumen, the second contacting surface of the distal end of the tube physically engages the first contacting surface of the catheter or stent such that force exerted axially on the tube along the tube channel axis exerts an axially-directed force on the second portion of the stent or catheter through contact between the second contacting surface of the tube and the first contacting surface of the catheter or stent reducing an effective column length of the stent or the catheter to the length of the second portion of the stent or catheter, thereby reducing buckling of the stent or catheter during advancement of the stent or catheter through the anatomical lumen for delivery of the catheter or stent to a target site.

2. The delivery system of claim 1, wherein a shape of the internal channel of the tube corresponds to an external shape of the first portion of the catheter or stent.

3. The delivery system of claim 1, wherein the second portion of the catheter or stent has a shape configured to anchor the second end of the catheter or stent in an anatomical cavity.

4. The delivery system of claim 3, wherein the second portion of the catheter or stent has a shape selected from the group consisting of: substantially cylindrical, substantially barbell, substantially trumpet-shaped, and substantially conical.

5. The delivery system of claim 1, further comprising a sheath having a proximal end and an inner diameter greater than an external diameter of the tube, the sheath inner diameter sized to receive all of the second portion of the catheter or stent therein, the proximal end of the sheath configured to receive the catheter or stent and tube.

6. The delivery system of claim 5, wherein the sheath further comprises a distal end having one or more slits or perforations configured to open upon sufficient force applied by the distal end of the second portion of the catheter or stent enabling the catheter or stent to exit the distal end of the sheath.

7. The delivery system of claim 5, wherein a distal end of the sheath comprises a radiopaque material.

8. The delivery system of claim 5, wherein at least the second portion of the catheter or stent is disposed within the sheath prior to deployment of the catheter or stent though a distal end of the sheath at a desired location in the anatomical lumen.

9. The delivery system of claim 5, wherein the catheter or stent is more compliant than the sheath.

10. The delivery system of claim 1, wherein the catheter or stent is more compliant than the tube.

11. The delivery system of claim 1, wherein the internal channel of the catheter or stent exhibits lubricious surface characteristics when wetted.

12. The delivery system of claim 1, wherein an outer surface of the catheter or stent exhibits lubricious surface characteristics when wetted.

13. The delivery system of claim 1, wherein the catheter or stent is a ureteral catheter or urethral catheter.

14. The delivery system of claim 1, wherein the catheter or stent is a ureteral stent or urethral stent.

15. The delivery system of claim 1, wherein the first portion of the catheter or stent further comprises an anchor portion disposed at the first end of the catheter or stent, the anchor portion configured to anchor the first end of the catheter or stent in an anatomical cavity.

16. The delivery system of claim 1, further comprising: a sheath having a proximal end, a distal end, and an inner diameter sized to receive at least the second portion of the catheter or stent therein, wherein the proximal end of the sheath is configured to receive the catheter or stent.

17. The delivery system of claim 16, wherein the stent or catheter and the sheath are configured such that at least the second portion of the catheter or stent is disposed within the sheath during axial advancement of the sheath and stent or catheter prior to deployment of the catheter or stent though a distal end of the sheath at a desired location in the anatomical lumen.

18. The delivery system of claim 16, wherein the distal end of the sheath comprises a radiopaque material.

19. The delivery system of claim 16, wherein the sheath is configured to be withdrawn after deployment of the catheter or stent while maintaining the catheter or stent in the anatomical lumen.

20. The delivery system of claim 16, wherein an elastic modulus of a material of the sheath is greater than an elastic modulus of a material of the catheter or stent.

21. The delivery system of claim 16, wherein the distal end of the sheath includes a distal end surface and one or more slits configured for deployment of the catheter or stent from the distal end of the sheath at a desired location in the anatomical lumen, the distal end of the sheath configured to maintain a closed configuration during axial advancement of the sheath and the catheter or stent through the anatomical lumen prior to deployment of the catheter or sheath and configured to enable opening of the distal end of the sheath during deployment by axial advancement of the catheter or stent relative to the sheath, thereby exerting force on the distal end surface of the sheath to open the one or more slits.

\* \* \* \* \*